US00PP16566P3

(12) United States Plant Patent
Khanuja et al.

(10) Patent No.: US PP16,566 P3
(45) Date of Patent: May 23, 2006

(54) MINT PLANT 'KUSHAL' FOR LATE TRANSPLANTING

(50) Latin Name: ***Mentha arvensis* L.**
Varietal Denomination: Kushal

(75) Inventors: Suman Preet Singh Khanuja, Lucknow (IN); Ajit Kumar Shasany, Lucknow (IN); Usha Yadav, Lucknow (IN); Sunita Dhawan, Lucknow (IN); Mahendra Pandurang Darokar, Lucknow (IN); Janak Raj Bahl, Lucknow (IN); Soni Gupta, Lucknow (IN); Sweta Pandey, Lucknow (IN); Anil Kumar Singh, Lucknow (IN); Ravi Prakash Bansal, Lucknow (IN); Raj Kishori Lal, Lucknow (IN); Om Parkash Dhawan, Lucknow (IN); Ali Arif Naqvi, Lucknow (IN); Alok Kaira, Lucknow (IN); Alok Krishna, Lucknow (IN); Virendra Kumar Singh Tomar, Lucknow (IN); Anil Kumar Singh, Lucknow (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/401,691

(22) Filed: Mar. 31, 2003

(65) Prior Publication Data

US 2004/0194176 P1 Sep. 30, 2004

(51) Int. Cl.
*A01H 5/00* (2006.01)

(52) U.S. Cl. ..... Plt./259
(58) Field of Classification Search ..... Plt./259
See application file for complete search history.

*Primary Examiner*—Anne Marie Grunberg
*Assistant Examiner*—June Hwu
(74) *Attorney, Agent, or Firm*—Foley & Lardner, LLP

(57) ABSTRACT

The present invention was related to the development of a novel, distinct high yielding plant with rapid regeneration ability obtained through screening of the somaclones in a methodical way for fast regeneration in the tissue culture stage itself which was achieved by inventing the plant 'Kushal'. The plant yield higher herbage with corresponding high essential oil when evaluated with available superior varieties of mint in late planting condition during April when the fields are vacated after the harvest of Rabi crop like wheat, chickpea, coriander etc. Further the suckers required for commercial vegetative planting can be produced even in low land condition as the plant is reasonably tolerant to water logging compared to the best check 'Kosi'.

3 Drawing Sheets

Genus and species of the plant claimed: *Mentha arvensis* L.

Variety denomination: 'Kushal'.

FIELD OF THE PRESENT INVENTION

The present invention is related to the development of a novel high yielding plant obtained through a unique method of screening of the somaclones in a methodical way for better regeneration. The selected plant establishes quickly in the field when shoot cuttings are planted much later than the normal planting time/season. The overall essential oil and menthol yield from the said plant is high compared to other existing varieties when planted late through shoot cuttings as transplanted mint. This plant is unique and clearly distinct from all other existing varieties of *Mentha arvensis* L. The new variety has been named as 'Kushal' which can be propagated vegetatively through suckers for commercial cultivation. All the experiment related to the development of the invented plant 'Kushal' were conducted at the farm of CIMAP, Lucknow, UP, India.

BACKGROUND AND PRIOR ART REFERENCES OF THE PRESENT INVENTION

*Mentha arvensis* Linn. Var *piperescens*. Holmes (methol or Japanese mint) is a highly valued industrial crop due to menthol, which is purified by crystallization through freezing from its essential oil. At CIMAP continuous improvement of the genotypes leading to betterment of different commercially important characters are underway. One of-the critical steps in menthol mint cultivation is the date of planting which determines the optimum yield of menthol after harvesting. In India the planting duration extends from mid of January to first quarter of February. Prior to planting the crop during this period, a small portion of land is used for sucker production during the month of September to January. During this period the underground suckers multiply vigorously which are used for planting in the main field.

But the sucker planting of mint during January and February (the normal planting time) interferes into the Rabi season crops like wheat, chickpea, coriander etc having a full grown crop stand at that time to be harvested at the mid to end of April. The Rabi cropping season starts at September-October to April-May. Planting in the month of January-February thus leads to the compromise for some of the Rabi harvest. The existing varieties of mints if planted late, i.e. in March-April show significant reduction in the biomass yield. In the varietal improvement programmes, the genetic alternations leading to enhancement in the menthol content in the essential oil and improving other adaptive characters determining the yield and quality of essential oil are most desirable.

So we planned experiments for developing a genotype which can be transplanted through stem cuttings instead of sucker planting after the Rabi harvest in mid April and also through sucker mode during normal planting in January-February without compromising on yield. The most desirable trait for such a genotype would be high and rapid regenerability of cuttings and that is what was achieved in the plant 'Kushal' of *Mentha arvensis.*

SUMMARY OF THE PRESENT INVENTION

The object of the present invention was to develop a novel high menthol producing plant through screening of the somaclones in a methodical way for better regeneration in the tissue culture stage itself which was achieved by inventing the plant 'Kushal'. The selected plant adapts quickly to the field condition when shoot cuttings are planted late than the normal planting duration. The essential oil yield from the said plant is high coupled with the property of being rich in menthol compared to other existing varieties when planted late from the shoot cuttings. This plant is unique and clearly distinct from all other existing varieties of *Mentha arvensis* L. The new variety has been named as 'Kushal' which can be propagated vegetatively through suckers for commercial cultivation. The suckers required for commercial vegetative planting can be produced even in water logging condition as the plant is tolerant to water logging compared to the best check Kosi.

'Kushal' is stable and reproduces true to type in successive generations of asexual reproduction.

BRIEF DESCRIPTION OF THE DRAWINGS

The accompanying colored photographs illustrate the overall appearance of the new mint plant 'Kushal' showing the colors as true as is reasonably possible with colored reproductions of this type. Color in the photographs may differ slightly from the color value cited in the detailed botanical description which accurately describes the color of 'Kushal'.

DETAILED DESCRIPTION OF THE PRESENT INVENTION

Figure 1:
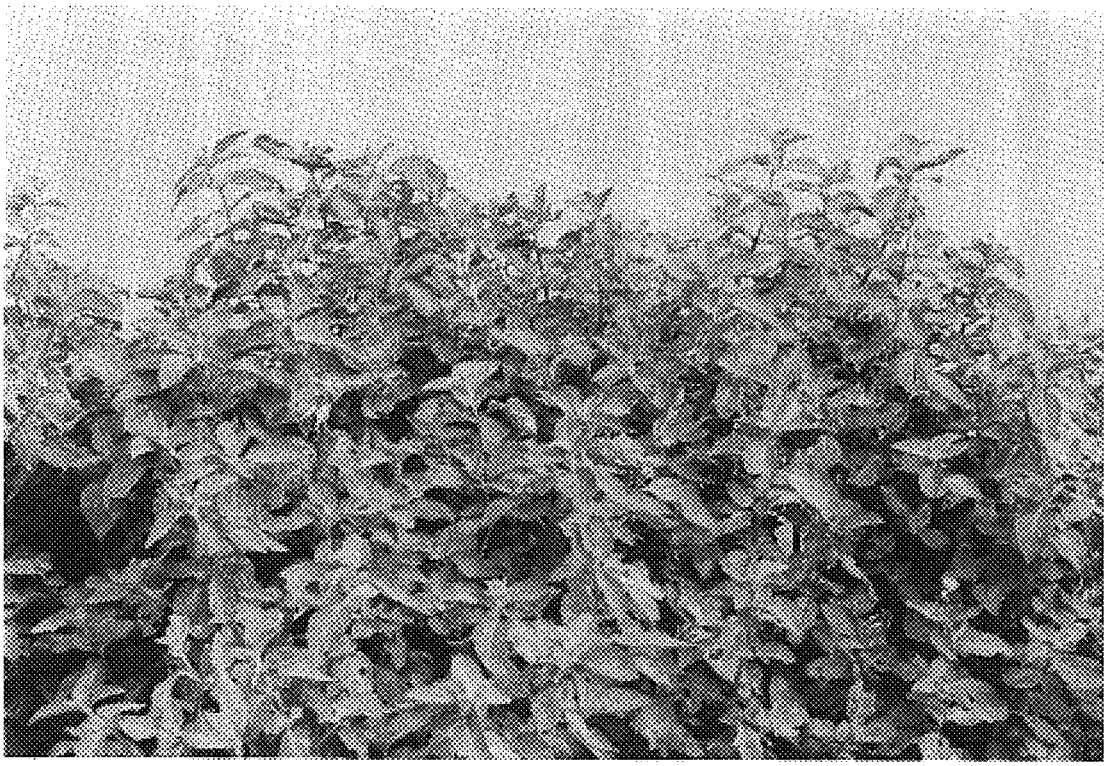
FIG. 1 is a colored photograph depicting a 'Kushal' plant (60 days after transplanting) in the field.
Figure 2:
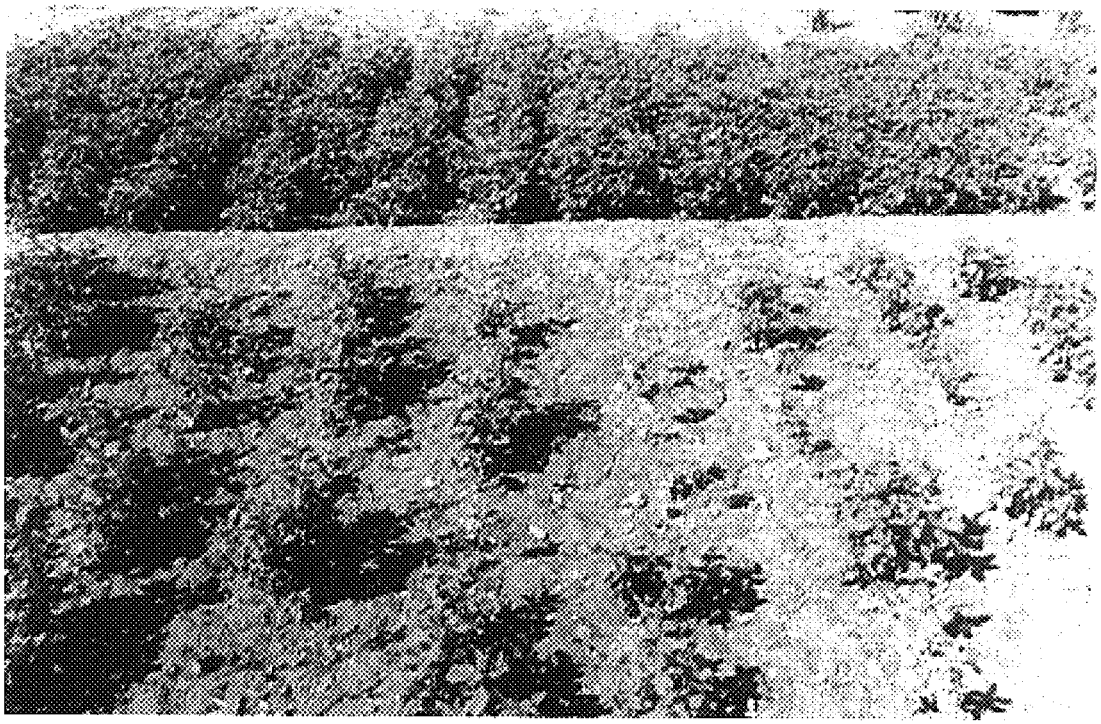
FIG. 2 is a colored photograph depicting the growth of field grown 'Kushal' plants (45 days after planting for sucker production) at the top of the photograph as compared to field grown 'Saksham' plants (45 days after planting for sucker production) at the bottom of photograph; both plants are in water logging conditions.
Figure 3:
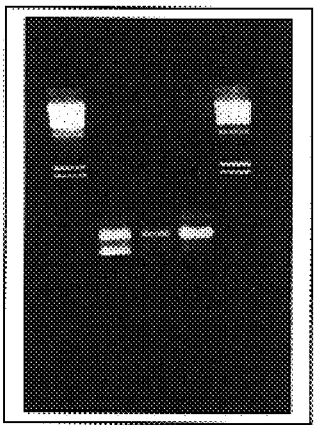
FIG. 3 is a black and white photograph depicting the RAPD profile of a 'Kushal' plant compared to a 'Himalaya' plant and 'Saksham' plant using primer CACCCTGCCGC (on the left) and primer CATCCCGAAC (on the right).
Figure 3:
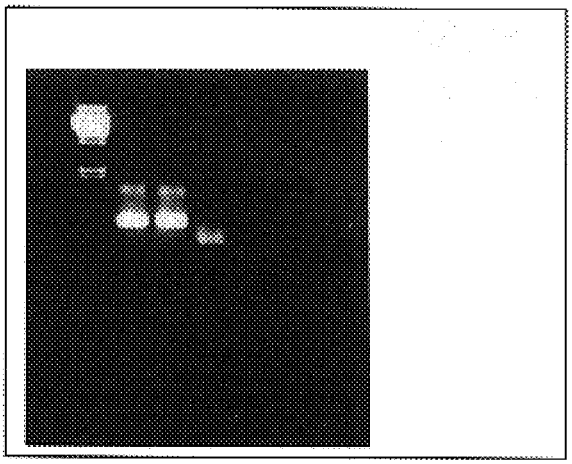

We used the plant 'Himalaya' PP 10935), an elite mint genotype for large scale screening of in vitro raised clones (Khanuja S P S, Shasany A K, Dhawan S, Sushil Kumar, 1998, Rapid procedure for isolating somaclones of altered genotypes in *Mentha arvensis.* J Medicinal and Aromatic Plant Sciences 20:359–361) to select clones with high regeneration capacity. Experiments were conducted using these clones for in vitro regenerability of shoot explants on MS based medium (Murashige T and Skoog F, 1962, A revised medium for rapid growth and bioassay with tobacco tissue cultures; *Physiol. Planta.* 15 473–497.). Passage transfers were repeatedly done at 15 days intervals for which every time the appearing shoots (after one month) were cut and inoculated afresh on the medium.

Out of about 1645 shoots screened 25 shoots showed the initiation of regeneration much earlier (fast growth as observed visually). After 20 passage transfers only one shoot (Clone M12), repeatedly demonstrated extra early initiation of regeneration followed by rapid growth compared to the other screened shoots. The internodal explants from these clone could show sign of shoot initiation from multiple sites within 7 days of inoculation compared to other clones showing regeneration much later. During passage transfers of the regenerated shoots the growth was rapid compared to the other clones as observed visually. The selected shoot was then multiplied in the medium described earlier (A. K. Shasany, S. p. s. Khanuja, S. Dhawan, U. Yadav, S. Sharma, S. Kumar, High regenerative nature of *Mentha arvensis* internodes. Journal of Biosciences 23 (1998) 641–646.).

The plantlets were hardened, transferred to the glasshouse and subsequently grown in the field for sucker production. This clone (M12) at this stage was designated as 'CIMAP/GRB 12'. The suckers produced were planted in the field of comparative field evaluation in initial field trails with other varieties in the last week of January as normal planting date for 2 consecutive years in RBD fashion and different growth and yield characteristics were recorded (Table I). For field trails 10m×10 m plots were prepared by adding only FYM 1.5 ton per ha and the crop was harvested 110 days after planting and the second harvesting was 70 after the first harvest.

TABLE 1

Comparative growth and yield characteristics of plant of invention 'CIMAP/GRB 12' in relation to the existing Japanese mint varieties (Average of field trials in the years 1999 and 2000) when planted during last week of January (normal planting time).

| Property | Himalaya | Kalka | Kosi | CIMAP/ GRB12 |
|---|---|---|---|---|
| Plant height (cm) | 60.9 ± 6.2 | 51.6 ± 2.7 | 66.2 ± 3.1 | 70.9 ± 0.7 |
| Canopy (cm) | 62–70 | 40–60 | 65–72 | 83–85 |
| Leaf number | 40.2 ± 4.2 | 38.0 ± 2.0 | 50.4 ± 3.8 | 41.0 ± 1.0 |
| Branch length | 40.4 ± 6.8 | 45 ± 9.7 | 52.0 ± 5.7 | 46.7 ± 0.9 |
| Branch number | 29.2 ± 4.0 | 27.2 ± 1.1 | 30.4 ± 1.7 | 32.0 ± 1.2 |
| Leaf length | 7.1 ± 0.5 | 7.4 ± 0.8 | 7.40 ± 0.7 | 7.75 ± 0.3 |
| Leaf breadth | 4.5 ± 0.2 | 4.0 ± 0.3 | 4.60 ± 0.5 | 4.8 ± 0.4 |
| Petiole length | 1.75 ± 0.3 | 1.5 ± 0.5 | 1.4 ± 0.3 | 1.5 ± 0.1 |
| Oil % | 0.7 | 0.8 | 0.8 | 0.8 |
| Menthol % | 80 | 82 | 76 | 78 |
| Herbage yield (Q per 100 $m^2$) | 1.25 | 0.80 | 1.70 | 1.72 |

A separate nursery was planted in February for April transplanting and subsequent evaluation. The plants produced were allowed to grow in the nursery till April and the stem cuttings of 20 to 40 cm were transplanted after filling, pulverizing the land. The overall objective was to develop a genotype amenable to planting late, with high yield of oil and menthol content through higher herbage production. The plant was tested in field trial for oil yield, menthol content and herbage production against the checks (varieties developed by CIMAP).

Replicated initial field trials were conducted following normal agronomic practices by planting shoot cuttings raised in the nursery in the month of April, 1999; bench scale field trial during 2000; and pilot scale field trials during 2001, 2002 in RBD fashion and different growth and yield characteristics were recorded. For initial field trials 10 m×10 m plots, for bench scale and pilot scale field trials 10 m×10 m plots were prepared by adding only FYM J.5 ton per ha. Astonishingly the plant 'CIMAP/GRB 12' (named as 'Kushal' at this stage) was able to out-compete all existing varieties in late planting.

TABLE 2

Comparative growth and yield characteristics of plant of invention 'Kushal' in relation to the existing Japanese mint varieties (Average of initial field trials in the years 1999 for late transplanting) when planted during April.

| Property | Himalaya | Kalka | Kosi | CIMAP/ GRB12 | LSD at 5% |
|---|---|---|---|---|---|
| Plant height (cm) | 109.7 ± 5.8 | 55.6 ± 2.9 | 86.7 ± 4.1 | 108.0 ± 1.3 | 19.6 |
| Oil % | 0.61 | 0.70 | 0.78 | 0.78 | 023 |
| Menthol % | 80 | 82 | 76 | 78 | 021 |
| Herbage yield (Q per 100 m2) | 3.25 | 1.42 | 2.50 | 3.30 | 0.60 |
| Oil yield (Kg per 100 $m^2$) | 1.78 | 1.01 | 1.75 | 2.33 | 0.54 |

TABLE 3

Comparative growth and yield characteristics of plant of invention 'Kushal' in relation to the existing Japanese mint varieties (Average of Bench scale field trials in the years 2000 for late transplanting) when planted during April.

| Genotypes | Plant height | Leaf-stem ratio | Oil content (%) | Herb Yield Q/ha (estimated) | Oil yield Kg/ha (estimated) |
|---|---|---|---|---|---|
| CIMAP/ GRB12 | 108.0 | 0.88 | 0.78 | 333 | 235.0 |
| Shivangi | 79.7 | 1.00 | 1.11 | 143 | 137.9 |
| Teesta | 87.3 | 0.86 | 0.80 | 174 | 126.9 |
| Saksham | 88.0 | 0.71 | 0.82 | 249 | 186.0 |
| Himalaya | 109.7 | 0.80 | 0.61 | 322 | 177.7 |
| Kosi | 86.7 | 0.92 | 0.78 | 249 | 174.4 |
| C.D. 5% | 19.6 | 0.37 | 0.23 | 62 | 54.0 |
| 1% | 26.0 | 0.50 | 0.31 | 83 | 71.9 |

In comparison to other mint plants, 'Kushal' differs genetically, yields more menthol when used as a transplanted mint, and the sucker is tolerant to water logging.

TABLE 4

Comparative growth and yield characteristics of plant of invention 'Kushal' in relation to the existing Japanese mint varieties (Average of pilot scale field trials in the years 2001 for late transplanting) when planted during April.

| Clones | Herb yield (q/ha) | Oil yield (kg/ha) (estimated) | Menthol yield (kg/ha) (estimated) |
|---|---|---|---|
| CIMAP/GRB12 | 328 | 221 | 177 |
| Shivalik | 236 | 128 | 98 |
| Himalya | 294 | 177 | 140 |
| Kasi | 318 | 185 | 147 |
| CD 5% | 62 | 50 | 40 |
| 1% | 92 | 67 | 53 |

TABLE 5

Comparative growth and yield characteristics of plant of invention 'Kushal' in relation to the existing Japanese mint varieties (Average of pilot scale field trials in the years 2002 for late transplanting) when planted during April.

| | Herb Yield (q/ha) (estimated) | Oil Yield (Kg/ha) (estimated) |
|---|---|---|
| CIMAP/GRB12 | 305 | 194 |
| Shivalik | 238 | 136 |
| Himalya | 270 | 163 |
| Kosi | 299 | 180 |

In all the field trials conducted for transplanted mint, 'CIMAP/GRB 12', now onwards referred as 'Kushal' performed better than all other mint varieties in terms of menthol and biomass (herbage) yield. The biomass yield of the genotype varied between 305 quintal per hectare (Q/ha) to 333 Q/ha. The menthol yield was in the range of 177 kilogram per hectare (kg/ha) to 194 kg/ha. So the plant 'Kushal' performed better than the best cheek varieties 'Saksham' (U.S. patent PP No. 3,279) and 'Kosi' (U.S. patent PP No. 12426) in all the field trial consistently when transplanted during the month of April (Table 2 to 5). This plant 'Kushal' also performed at par in total biomass (herbage) yield compared to the best control variety 'Kosi' when planted in the month of February, which is the normal month of planting of mints.

Interestingly, another most important character was encountered by us in the year 2001 when the sucker producing plots fields at CIMAP farm were submerged due to untimely rains. At the initial stage of plantation when the fields were submerged with water for a Longer duration (more than 7 days) then all other varieties did not regenerate as maximum plants and suckers in the soil were damaged due to lack of aeration. The sucker fields for other varieties became patchy with poor growth where as the plant 'Kushal' was not affected in terms of growth parameters. So, experiment was conducted in the next year by logging the fields with water for sucker production and observations (Table 6) were recorded. As observed from the experiment, the plant 'Kushal' can withstand water logging, whereas the survival, growth and proliferation of other varieties were severely hampered leading to less and week sucker yield.

TABLE 6

Observations recorded in the I $m^2$ area during the month of September 2002 in the mint variety Kushal (Date Sep. 15, 2002)

| | Survival % | | | Plant height (cm) | | |
|---|---|---|---|---|---|---|
| Sino | Kushal | Sak-sham | Kosi | Kushal | Saksham | Kosi |
| 1. | 100 | 50 | 3 | 30 | 15 | 10 |
| 2. | 100 | 40 | 20 | 25 | 26 | 15 |
| 3. | 90 | 50 | 28 | 30 | 20 | 10 |
| 4. | 100 | 50 | 32 | 35 | 15 | 16 |
| 5. | 100 | 30 | 20 | 30 | 17 | 15 |
| 6. | 100 | 40 | 30 | 28 | 20 | 18 |
| 7. | 90 | 52 | 34 | 30 | 16 | 15 |
| 8. | 92 | 50 | 30 | 35 | 18 | 16 |
| 9. | 96 | 52 | 36 | 30 | 22 | 12 |
| 10. | 100 | 56 | 40 | 36 | 20 | 15 |
| 11. | 100 | 60 | 30 | 32 | 18 | 17 |
| 12. | 94 | 40 | 28 | 26 | 24 | 20 |
| S.E. ± | 1.166 | 2.311 | 1.589 | 0.905 | 0.958 | 0.829 |

| | Primary branches/Plant | | |
|---|---|---|---|
| Sino | Kushal | Saksham | Kosi |
| 1. | 7 | 5 | 3 |
| 2. | 8 | 8 | 4 |
| 3. | 7 | 5 | 4 |
| 4. | 9 | 6 | 5 |
| 5. | 12 | 7 | 6 |
| 6. | 10 | 8 | 5 |
| 7. | 6 | 5 | 6 |
| 8. | 7 | 4 | 5 |
| 9. | 10 | 5 | 5 |
| 10. | 12 | 9 | 4 |
| 11. | 8 | 5 | 8 |
| 12. | 12 | 10 | 5 |
| S.E. ± | 0.601 | 0.533 | 0.354 |

Taxonomic description of the mint plant 'Kushal':

1. *Genus.*—*Mentha.*
2. *Species.*—*arvensis* L.
3. *Family.*—Lamiaceae.
4. *Common name.*—Japanese mint/com mint/menthol mint.
5. *Plant height.*—70.0 to 108.0 cm.
6. *Plant canopy.*—83–85 cm.
7. *Growth habit.*—Erect sturdy main stem, profuse branching.
8. *Stem.*—Round to quadrangular hard, woody, green (144A), 5–11 mm thick at 5th internode; scabridulous surface texture.
9. *Leaf.*—Colour Upper surface light green (137B); lower surface olive green (138B). Texture: Moderately thick and rigid. Surface: Hairy and rough. Shape: Lacerate. Margin: Moderately deep serration (18 to 50 number). Tip: Acute. Base: Attenuate. Size: Moderately broad. Petiole length: 1.5±0.1 cm. Area: 6.0 $cm^2$ (Average of full branch). Length: 7.75±0.3 cm. Width: 4.8±0.4 cm.
10. *Fresh weight of leaf.*—Fresh weight of stem ratio (w/w): 0.88 to 1.54 g.
11. *Inflorescence.*—Indefinite recemose. Total number of florets 20 to 40.
12. *Flowers.*—Campanulate flower, arranged in whorls surrounding the stem at the base of lateral leaves. Flower length (mm): 3.50. Flower diameter (mm): 2–3. Pedicel Yellow green (145C); average diameter 1 mm; Surface texture scabrid. Peduncle: 0.5 mm diameter; surface texture scabrid; Average length 2 mm; color light green (138C). Calyx: Four, Yellow green (143C): oblanceolate shape; 1 mm×0.5 mm in size. Corolla: Pinkish white, four, fused to a bell shaped. Corolla tube (56C); 2 mm×2.5 mm in size. Anthers: Four, ocidimetary, come out of the corolla tube; 0.5 mm in size; white in color (155C). Filaments: 0.5 mm in length; white in color (155C). Stigma: Bifid, Purple (76A). Style: 2.5 mm in length; pinkish white color (56C).
13. *Oil content in the fresh herb* (%).—0.7 to 0.9.
14. *Oil quality.*—Menthol content (%): 77 to 781. Congealing point: 20 to 21° C.
15. *Herbage*(*shoot biomass*). —Q/100 $m^2$: 1.72 to 3.33.

In addition to producing more herbage and essential oil comparatively, the plant 'Kushal' adopts quickly to late planting condition. Water logging condition during sucker production does not hamper the survival, growth and proliferation of the plant. The plant of invention 'Kushal' produces herbage comparable to the improved variety 'Kosi' if planted in the month of January (normal date of planting) (Table 1). But in late planting during April the plant 'Kushal' surpasses the growth, yield of herbage and oil to any other existing varieties (Table 2). 'Kushal' produces more herbage and more essential oil compared to the most improved variety 'Kosi' (now cultivated widely in mint growing regions of India) when planted late.

From the parent plant 'Himalaya' the new plant of invention is far ahead in terms of herbage and essential oil yield when planted in either January or April. So, as per the objective we could select a plant type which can be planted in the month of April if the main field after the harvesting of Rabi crop. Generally the land after the harvest of wheat chickpea is left as fallow till the next planting of rice crop during rainy season (Khariff). Otherwise a short duration crop is planted within this period which may yield low income to the farmer. Instead if a crop of mint is harvested during this period the farmers or the landowner will be benefited immensely as mint is a cash crop. Improved plant type with adaptability to late planting combined with better yield of herbage, essential oil and ultimately menthol in the plant of invention 'Kushal' can enhance the income of the planter in long run.

TABLE 7

Additional description of 'Kushal' compared to the parent 'Himalaya'

| | Character | cv. Himalaya | cv. Kushal |
|---|---|---|---|
| 1. | Leaf:stem ratio | 1.0 | 1.54 |
| 2. | Stem | | |
| | colour | Green(143C) | Green (144A) |
| | lower stem colour | purplish(70A) | |
| | Stiffness | Hard | Hard |
| | Thickness at 5th internode(mm) | 8.0 | 11 |
| 3. | Leaf | | |
| | colour | Green(138B) | Green (137B) |
| | Length(cm) | 7.1 | 7.75 |
| | Width(cm) | 4.5 | 4.8 |
| | Area($cm^2$) | 15.4 to 18.0 | 15.2–19.0 |
| 4. | Petiole length (cm) | 1.5 | 2.2 |
| 5. | Flower colour | Pinkish white (56C) | Pinkish white (56C) |
| 6. | Flower length (mm) | 3.72 | 3.50 |
| 7. | Calyx colour | Green (143C) | Green (143C) |
| 8. | Stigma colour | White | Purplish white (76A) |
| 9. | Disease incidence to | | |
| | Rust | Resistant | Resistant |
| | Alternaria leaf blight | Resistant | Resistant |
| | Corynespora leaf spot | Tolerant | Tolerant |
| | Powdery mildew | Tolerant | Tolerant |

Evidence of Uniformity and Stability

No variants of any kind (morphological or molecular) have been observed since 1998 (the year of development) and through yield trials in the following years indicating the stability and uniformity of the genotype. Further, the comparative total herbage, oil and ultimately menthol yields of 'Kushal' were significantly higher in comparison to the parent variety 'Himalaya', the high menthol yielding variety 'Kalka' (CIMAP/HY77), and best variety check 'Kosi' in different years and seasons. The traits of improved herbage, essential of yield and the adaptability to late transplanting is unprecedented and stable.

Statement of Distinction

The genotype 'Kushal' possessing the traits of increased adaptability to late transplanting combined with higher essential oil and herbage yield, is unique and unprecedented not possessed by any known variety. The genotype is having higher biomass and higher oil yield unit area in comparison to others. Its genetic make up is distinct in terms of the DNA profile.

The colour codes are in accordance with The R.H.S. Colour Chart published by The Royal Horticultural Society, 80 Vincent Square, London SW1P 2PE, 1995.

Randomly Amplified Polymorphic DNA analysis: The RAPD profiles of the plant 'Kushal' were unambiguously able to establish its distinct identity as completely different from the parent plant 'Himalaya' as well as the known released varieties. The plant of the present invention was developed by screening molecular variants among somaclones already differentiated as distinct, unique and novel at DNA level. The plant is having desirable morphological and economical traits in a rare unmatchable combination and is available only with us at CIMAP. No variation in the RAPD patterns was observed in the analysis of the micropropagated as well as field raised population in successive generations indicating the stability of the genotype. The 20 MAP primers (MAP 01 to MAP 20) synthesized in the laboratory using ABI 392 DNA synthesizer, with the sequence AAATCGGAGC (SEQ ID NO: 1), GTCCTACTCG (SEQ ID NO: 2), GTCCTTAGCG (SEQ ID NO: 3), TGCGCGATCG (SEQ ID NO: 4), AACGTACGCG (SEQ ID NO: 5), GCACGCCGGA (SEQ ID NO:6), CACCCTGCGC (SEQ ID NO: 7), CTATCGCCGC (SEQ ID NO: 8), CGGGATCCGC (SEQ ID NO: 9), GCGAATTCCG (SEQ ID NO: 10), CCCTGCAGGC (SEQ ID NO: 11), CCAAGCTTGC (SEQ ID NO: 12), GTGCAATGAG (SEQ ID NO: 13), AGGATACGTG (SEQ ID NO: 14), AAGATAGCGG (SEQ ID NO: 15), GGATCTGAAC (SEQ ID NO: 16), TTGTCTCAGG (SEQ ID NO: 17), CATCCCGAAC (SEQ ID NO: 18), GGACTCCACG (SEQ ID NO: 19), AGCCTGACGC (SEQ ID NO: 20) were used for the analysis to develop the unique fingerprint pattern. Accordingly the invention provides a new and distinct mint plant of *Mentha arvensis* 'Kushal', developed through tissue culture, possessing the following combination of characters:

a. the said plant is able to adopt quickly to late planting condition and produce higher herbage and essential oil compared to the existing varieties, b. the plant is suitable for transplanting using grown shoots in April as well as normal planting through suckers in the month February, c. the said plant produces high essential oil yield (0.7 to 0.9%) as well as herbage yield (1.72 to 3.33 Q per 100 $m^2$), d. the said plant possesses better growth and vegetative growth with high regenerability covering at least 83–85 cm canopy area and a height of at least 70.0 to 108.0 cm in a maximum of 110 days, e. the said plant has distinct molecular profile by random amplified polymorphic DNA (RAPD) using 20 random primers distinguishing the plant from the other existing varieties.

f. the said plant retains the characteristics of tolerance to leaf spot, rust and powdery mildew as in the parent variety 'Himalaya', g. the said plant has light greenish leaves(138B), pinkish white flowers (56C) like the parent plant 'Himalaya' but green stem (144A), h. the plant genotype 'Kushal' withstand waterlogging condition during sucker production in terms of survival, growth compared to other varieties checked.

SEQUENCE LISTING

```
<160> NUMBER OF SEQ ID NOS: 20

<210> SEQ ID NO 1
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1

aaatcggagc                                                          10


<210> SEQ ID NO 2
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2

gtcctactcg                                                          10


<210> SEQ ID NO 3
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3

gtccttagcg                                                          10
```

-continued

<210> SEQ ID NO 4
<211> LENGTH: 10
<212> TYPE: DNA
<213> ORGANISM: Artificial Sequence
<220> FEATURE:
<223> OTHER INFORMATION: Description of Artificial Sequence: Synthetic
primer

<400> SEQUENCE: 4 tgcgcgatcg 10

<210> SEQ ID NO 5
<211> LENGTH: 10
<212> TYPE: DNA
<213> ORGANISM: Artificial Sequence
<220> FEATURE:
<223> OTHER INFORMATION: Description of Artificial Sequence: Synthetic
primer

<400> SEQUENCE: 5 aacgtacgcg 10

<210> SEQ ID NO 6
<211> LENGTH: 10
<212> TYPE: DNA
<213> ORGANISM: Artificial Sequence
<220> FEATURE:
<223> OTHER INFORMATION: Description of Artificial Sequence: Synthetic
primer

<400> SEQUENCE: 6 gcacgccgga 10

<210> SEQ ID NO 7
<211> LENGTH: 10
<212> TYPE: DNA
<213> ORGANISM: Artificial Sequence
<220> FEATURE:
<223> OTHER INFORMATION: Description of Artificial Sequence: Synthetic
primer

<400> SEQUENCE: 7 caccctgcgc 10

<210> SEQ ID NO 8
<211> LENGTH: 10
<212> TYPE: DNA
<213> ORGANISM: Artificial Sequence
<220> FEATURE:
<223> OTHER INFORMATION: Description of Artificial Sequence: Synthetic
primer

<400> SEQUENCE: 8 ctatcgccgc 10

<210> SEQ ID NO 9
<211> LENGTH: 10
<212> TYPE: DNA
<213> ORGANISM: Artificial Sequence
<220> FEATURE:
<223> OTHER INFORMATION: Description of Artificial Sequence: Synthetic
primer

<400> SEQUENCE: 9 cgggatccgc 10

-continued

<210> SEQ ID NO 10
<211> LENGTH: 10
<212> TYPE: DNA
<213> ORGANISM: Artificial Sequence
<220> FEATURE:
<223> OTHER INFORMATION: Description of Artificial Sequence: Synthetic
primer

<400> SEQUENCE: 10 gcgaattccg 10

<210> SEQ ID NO 11
<211> LENGTH: 10
<212> TYPE: DNA
<213> ORGANISM: Artificial Sequence
<220> FEATURE:
<223> OTHER INFORMATION: Description of Artificial Sequence: Synthetic
primer

<400> SEQUENCE: 11 ccctgcaggc 10

<210> SEQ ID NO 12
<211> LENGTH: 10
<212> TYPE: DNA
<213> ORGANISM: Artificial Sequence
<220> FEATURE:
<223> OTHER INFORMATION: Description of Artificial Sequence: Synthetic
primer

<400> SEQUENCE: 12 ccaagcttgc 10

<210> SEQ ID NO 13
<211> LENGTH: 10
<212> TYPE: DNA
<213> ORGANISM: Artificial Sequence
<220> FEATURE:
<223> OTHER INFORMATION: Description of Artificial Sequence: Synthetic
primer

<400> SEQUENCE: 13 gtgcaatgag 10

<210> SEQ ID NO 14
<211> LENGTH: 10
<212> TYPE: DNA
<213> ORGANISM: Artificial Sequence
<220> FEATURE:
<223> OTHER INFORMATION: Description of Artificial Sequence: Synthetic
primer

<400> SEQUENCE: 14 aggatacgtg 10

<210> SEQ ID NO 15
<211> LENGTH: 10
<212> TYPE: DNA
<213> ORGANISM: Artificial Sequence
<220> FEATURE:
<223> OTHER INFORMATION: Description of Artificial Sequence: Synthetic
primer

<400> SEQUENCE: 15 aagatagcgg 10

-continued

```
<210> SEQ ID NO 16
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16

ggatctgaac                                                          10


<210> SEQ ID NO 17
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17

ttgtctcagg                                                          10


<210> SEQ ID NO 18
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18

catcccgaac                                                          10


<210> SEQ ID NO 19
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19

ggactccacg                                                          10


<210> SEQ ID NO 20
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20

agcctgacgc                                                          10
```

I claim:

1. A new and distinct *Mentha arvensis* plant named ‘Kushal’, developed through tissue culture as shown and described.

* * * * *

The difference in the DNA profile of Kushal from the parent Himalaya was observed with the following primers.

CACCCTGCGC

Lane 1 and 5: λ Hind III Marker
Lane 2: Profile of Himalaya
Lane 3: Profile of Saksham
Lane 4: Profile of Kushal

CATCCCGAAC

Lane 1: λ Hind III Marker
Lane 2: Profile of Himalaya
Lane 3: Profile of Saksham
Lane 4: Profile of Kushal